DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED SEPTEMBER 3, 1974

926 O.G. 12

T926,013
DIMETHYL 5-BROMOISOPHTHALATE
Benjamin Thompson, 2204 Montrose Drive,
Kingsport, Tenn. 37664
Filed Feb. 22, 1974, Ser. No. 444,938
Int. Cl. C07c *69/80*
U.S. Cl. 260—475 R
No Drawing. 3 Pages Specification

This invention relates to dimethyl 5-bromoisophthalate, which is useful as an intermediate in the preparation of monomers, such as 5-(4-sodiosulfophenoxy) isophthalate, said monomers being used to impart basic dyeability to polyester fibers.